(12) United States Patent
McLeod

(10) Patent No.: US 10,321,839 B2
(45) Date of Patent: Jun. 18, 2019

(54) LEAD CABLE FOR ELECTROCARDIOGRAPH SYSTEMS

(71) Applicant: General Electric Company, Schenectady, NY (US)

(72) Inventor: Michael P. McLeod, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 77 days.

(21) Appl. No.: 15/087,017

(22) Filed: Mar. 31, 2016

(65) Prior Publication Data

US 2017/0281040 A1 Oct. 5, 2017

(51) Int. Cl.
*A61B 5/0428* (2006.01)

(52) U.S. Cl.
CPC ...... *A61B 5/04286* (2013.01); *A61B 2562/12* (2013.01); *A61B 2562/222* (2013.01); *A61B 2562/227* (2013.01)

(58) Field of Classification Search
CPC ........ A61N 1/05; A61N 1/0563; A61N 1/056; A61B 5/042
USPC .................................................. 607/122, 116
See application file for complete search history.

(56) References Cited

U.S. PATENT DOCUMENTS

| 5,899,774 A | 5/1999 | Sexton | |
|---|---|---|---|
| 2010/0114279 A1* | 5/2010 | Strandberg | A61N 1/05 607/116 |
| 2010/0305675 A1* | 12/2010 | Laske | A61N 1/0534 607/122 |
| 2011/0079423 A1* | 4/2011 | Zhao | A61N 1/056 174/5 R |

* cited by examiner

*Primary Examiner* — Jon Eric C Morales
(74) *Attorney, Agent, or Firm* — Dean D. Small; The Small Patent Law Group, LLC

(57) ABSTRACT

An electrocardiogram system is provided. The system includes an array of sensors configured to generate electrical signals relating to cardiac activity. The system further includes a plurality of lead cables. Each lead cable includes a sensor terminal, an opposing sensor terminal, and an intermediate segment. The intermediate segment is interposed between the sensor terminal and the opposing sensor terminal. The array of sensors are electrically coupled to the sensor terminals. The intermediate segment is configured to carry the electrical signals from the sensor terminal to the opposing sensor terminal. The intermediate segment is enclosed by a non-conductive enclosure. The non-conductive enclosure having opposing linear surfaces and opposing lateral surfaces extending from the opposing linear surfaces. The opposing linear surfaces are parallel with respect to each other.

23 Claims, 6 Drawing Sheets

LEAD CABLE FOR ELECTROCARDIOGRAPH SYSTEMS

FIELD

Embodiments described herein generally relate to an interconnect for coupling an array of sensors with an electrocardiograph system.

BACKGROUND OF THE INVENTION

A conventional electrocardiograph (ECG) system is a cardiac diagnostic/monitoring system adapted to record the electrical activity of a patient's heart. Hospitals and clinics commonly implement ECG's to monitor and diagnose patients, which may include different diagnostic applications such as resting ECG, stress testing ECG, and cardiac defibrillators.

The ECG generally includes an array of sensors or transducers placed at predetermined positions on a patient's body. The recorded data from the ECG is generally displayed in the form of a graph that is often referred to as an electrocardiogram generated by the ECG system. The array of sensors are connected to the conventional ECG system via a series of lead cables that have a cylindrical shape. Each lead cable electrically connects one of the sensors to the conventional ECG system. However, due to the length and number of the lead cables, the lead cables may get twisted or knotted with each other restricting movement of the sensors.

Thus, for at least the reasons described above a need exists for an improved lead cable.

BRIEF DESCRIPTION OF THE INVENTION

In one embodiment, a lead cable is provided. The lead cable includes a sensor terminal segment that includes a sensor terminal. The sensor terminal is configured to be electrically coupled to an electrocardiogram sensor. The lead cable further includes a combiner terminal segment that includes an opposing sensor terminal and a shield terminal. The lead cable also includes an intermediate segment interposed between the sensor terminal segment and the combiner terminal segment. The intermediate segment is configured to carry electrical signals generated by the electrocardiogram sensor from the sensor terminal to the opposing sensor terminal. The lead cable further includes non-conductive enclosure configured to house the intermediate segment. The non-conductive enclosure having opposing linear surfaces and opposing lateral surfaces extending from the opposing linear surfaces. The opposing linear surfaces are parallel with respect to each other.

In an alternative embodiment, a system (e.g., an electrocardiogram system) is provided. The system includes an array of sensors configured to generate electrical signals relating to cardiac activity. The system further includes a plurality of lead cables. Each lead cable includes a sensor terminal, an opposing sensor terminal, and an intermediate segment. The intermediate segment is interposed between the sensor terminal and the opposing sensor terminal. The array of sensors are electrically coupled to the sensor terminals. The intermediate segment is configured to carry the electrical signals from the sensor terminal to the opposing sensor terminal. The intermediate segment is enclosed by a non-conductive enclosure. The non-conductive enclosure having opposing linear surfaces and opposing lateral surfaces extending from the opposing linear surfaces. The opposing linear surfaces are parallel with respect to each other.

In an alternative embodiment, a method (e.g., method for manufacturing a lead cable for an electrocardiogram system) is provided. The method includes providing a sensor conductor enclosed by a dielectric. The sensor conductor is configured to carry an electrical signal related to cardiac activity generated by a sensor. The method also includes surrounding the dielectric with a shield conductor. The dielectric is interposed between the dielectric and the shield conductor. The method further includes enclosing the shield conductor with a non-conductive enclosure. The non-conductive enclosure includes opposing linear surfaces and opposing lateral surfaces extending from the opposing linear surfaces. The opposing linear surfaces are in parallel with respect to each other.

DETAILED DESCRIPTION OF THE INVENTION

Figure 1:
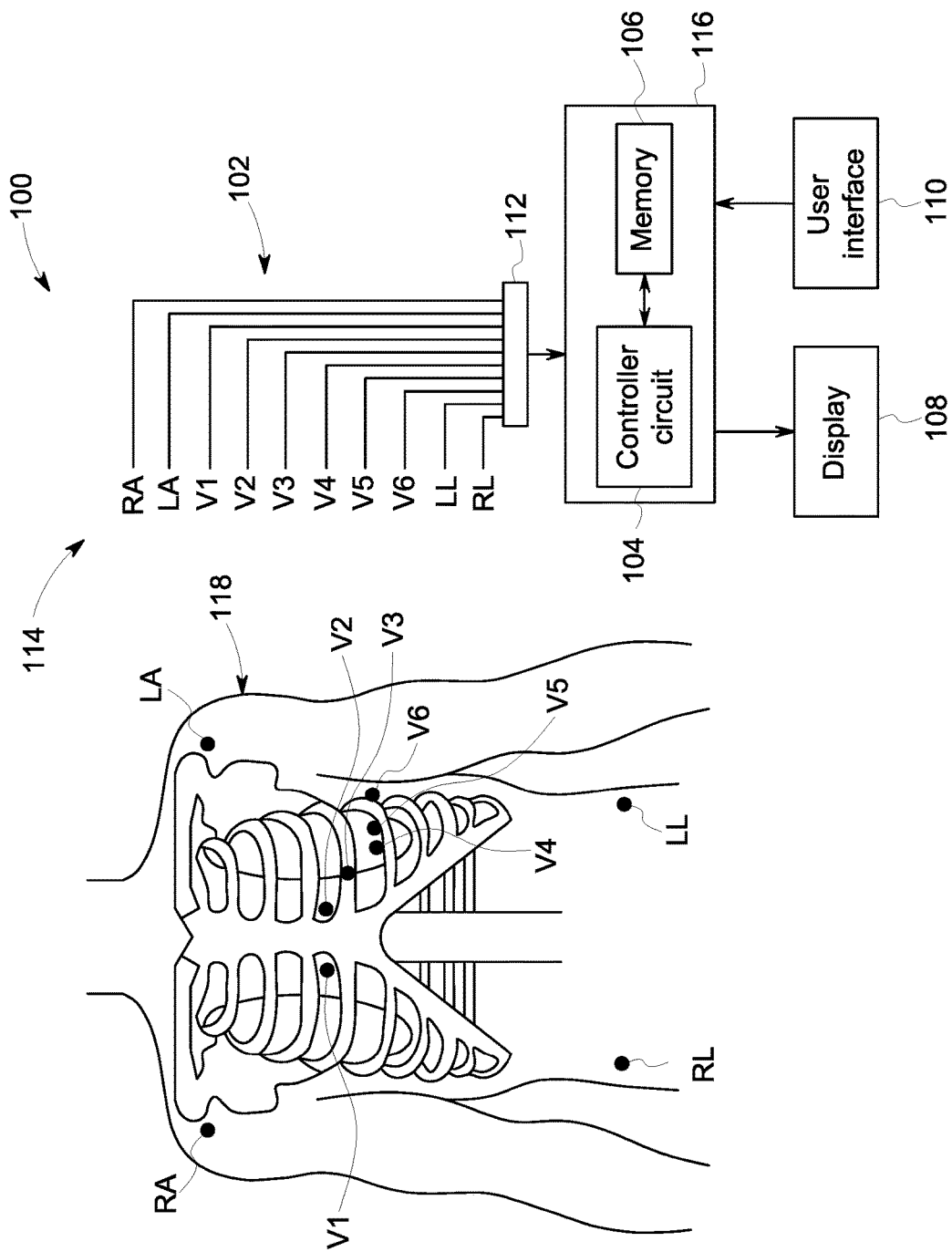
FIG. 1 illustrates a schematic illustration of an electrocardiograph system, in accordance with an embodiment.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for a lead cable of an electrocardiograph (ECG) system. The lead cable may have opposing linear surfaces. The opposing linear surfaces form an electrical lead cable or wire that has opposing flat surfaces. The lead cable is configured to communicate or transfer signals from ECG electrodes or transducers on a patient (e.g., on a surface of the patient) to the ECG system to record or display the measured cardiac information. A technical effect of the shape of the electrical lead cable reduces tangling when multiple cables are used side by side in combination relative to cylindrical electrical lead cables.

FIG. 1 illustrates a schematic illustration of an electrocardiograph (ECG) system 100, in accordance with an embodiment. The ECG system 100 is configured to measure one or more electrical signals representing cardiac activity of a patient 118. The ECG system 100 is electrically and/or physically coupled to the patient 118 by an array of sensors or transducers 114. The ECG system 100 may include a controller circuit 104, a memory device 106, a display 108, and a user interface 110. Optionally, one or more components of the ECG system 100 may be enclosed within a housing 116.

The controller circuit 104 may be configured to receive and process the acquired ECG data from the sensors 114. For example, the controller circuit 104 may process or analyze the ECG data (e.g., based on executable instructions stored on the memory device 106) in any known manner to facilitate patient diagnosis. The controller circuit 104 may include one or more processors. Optionally, the controller circuit 104 may include a central controller circuit (CPU), one or more microprocessors, a graphics controller circuit (GPU), or any other electronic component capable of processing inputted data according to specific logical instructions. Additionally or alternatively, the controller circuit 104 may execute instructions stored on a tangible and non-transitory computer readable medium (e.g., the memory device 106). The controller circuit 104 may store the processed ECG data to the memory device 106 for storage, and/or the display 108 for communication to a user. Optionally, the processed ECG may be represented on the display 108 in a graphical form referred to as an electrocardiogram.

The memory device 106 may be used for storing processed ECG data, firmware or software corresponding to, for example, a graphical user interface, one or more algorithms for processing ECG data, programmed instructions (e.g., for the controller circuit 104), and/or the like. The memory 140 may be a tangible and non-transitory computer readable medium such as flash memory, RAM, ROM, EEPROM, and/or the like.

The controller circuit 104 is operably coupled to the display 108 and the user interface 110. The display 108 may include one or more liquid crystal displays (e.g., light emitting diode (LED) backlight), organic light emitting diode (OLED) displays, plasma displays, CRT displays, and/or the like. The display 108 may display patient information, the electrocardiogram (e.g., graphically, numeral values, and/or the like), measurements, diagnosis, treatment information, and/or the like received by the display 108 from the controller circuit 104.

The user interface 110 controls operations of the controller circuit 104 and is configured to receive inputs from the user. The user interface 110 may include a keyboard, a mouse, a touchpad, one or more physical buttons, and/or the like. Optionally, the display 108 may be a touch screen display, which includes at least a portion of the user interface 110.

In the illustrated embodiment, the array of sensors 114 include a right arm electrode RA; a left arm electrode LA; chest electrodes V1, V2, V3, V4, V5 and V6; a right leg electrode RL; and a left electrode leg LL for acquiring a standard twelve lead, ten-electrode electrocardiogram signal. FIG. 1 illustrates positions of the array of sensors 114 relative to the patient 118 for acquiring cardiac activity or ECG data. The twelve leads include leads I, II, V1, V2, V3, V4, V5 and V6 which can be acquired directly from the patient leads, and leads III, aVR, aVL and aVF which can be derived using Einthoven's law. In other embodiments, alternative configurations of sensors and sensor locations can be used to acquire a standard or non-standard ECG signal. Alternatively, other ECG acquisition devices and configurations may be implemented Each lead cable 102 may be electrically and/or physically coupled to a corresponding sensor 114 that measures or acquires electrical characteristics (e.g., voltage, electrical potential) of the patient 118 proximate to the sensor 114. Over time, the electrical characteristic forms an electrical signal that corresponds to or relates to cardiac activity of the patient 118. For example, the electrical characteristics may define an amplitude, frequency, and/or the like of the electrical signal. The electrical signal generated by the sensors 114 may be received by the controller circuit 104 via the series of lead cables 102. For example, the lead cables 102 carry the electrical signals from the sensors 114 to the controller circuit 104 via a combiner connector 112. The combiner connector 112 may operably couple the sensors 114 to the controller circuit 104.

In operation, the combiner connector 112 may combine the electrical characteristics of one or more differential pairs of the lead cables 102. In various embodiments, at least a portion of the lead cables 102 may have corresponding complementary sensors 114 representing a differential pair. The combiner connector 112 may combine each pair of the electrical signals and transmit the combined pairs to the controller circuit 104. For example, the ECG system 100 may have ten lead cables 102 that correspond to five differential pairs. The combiner connector 112 may combine (e.g., add, subtract) the electrical signals of each pair to form a combined pair electrical signals. For example, the combiner connector 112 may combine the pairs of the ten lead cables 102 to determine five combined pair electrical signals, which are received by the controller circuit 104.

Figure 2A:
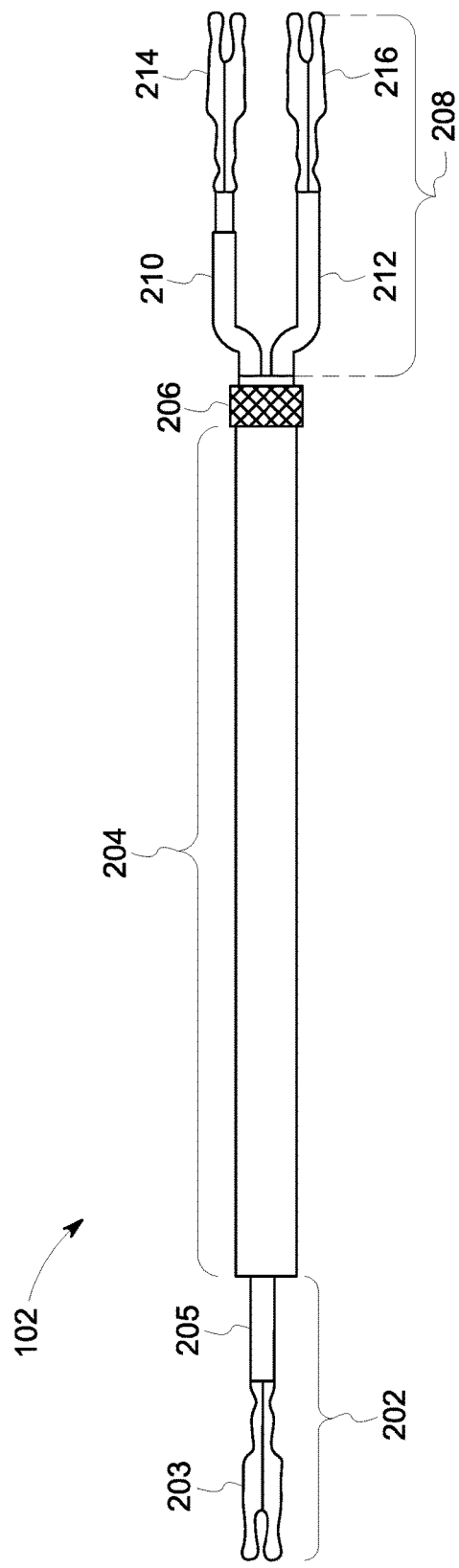
FIG. 2A illustrate a top view of a lead cable of the electrocardiograph system shown in FIG. 1, in accordance with an embodiment.
Figure 2B:
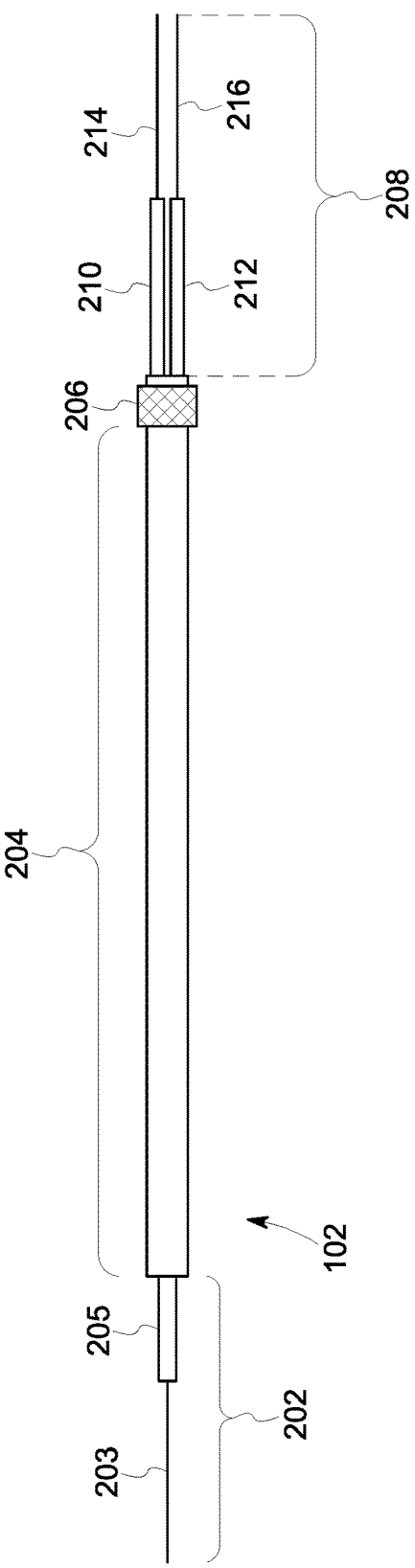
FIG. 2B illustrate a side view of a lead cable of the electrocardiograph system shown in FIG. 1, in accordance with an embodiment.

FIGS. 2A-B illustrate a top view and a side view of a lead cable 200 of the ECG system 100, in accordance with an embodiment. For example, the lead cable 200 may be similar to or the same as one of the lead cables 102 shown in FIG. 1. The lead cable 200 includes the sensor terminal segment 202, an intermediate segment 204, and a combiner terminal segment 208. The sensor terminal segment 202 may electrically and/or physically couple the lead cable 200 to one of the sensors 114. It may be noted that the lead cable 200 may be configured to be in accordance with Title 21 C.F.R. Section Part 898 entitled Performance Standard for Electrode Lead Wire and Patient Cables.

The combiner terminal segment 208 may electrically and/or physically couple the lead cable 200 to the combiner connector 112. The lead cable 200 may include two electrically conductive components that extend along the lead cable 200. One of the conductive components (e.g., sensor conductor 302 shown in FIG. 3) may carry or transfer electrical characteristics measured by one of the sensors 114 from the sensor terminal segment 202 to the combiner terminal segment 208.

The sensor terminal segment 202 includes the sensor terminal 203 and a shield segment 205. Optionally, the sensor terminal segment 202 may be enclosed in a housing (not shown) that is configured to physically couple the sensor terminal segment 202 to one of the sensors 114. The sensor terminal 203 may include a conductive metal (e.g., nickel, copper, gold, silver, tin, conductive alloy, and/or the like) corresponding to one of the conductors (e.g., sensor conductor 302 shown in FIG. 3) within the lead cable 200. For example, the conductive metal may extend a length of the lead cable 200 from the sensor terminal 203 to an opposing sensor terminal 214.

The shield segment 205 of the sensor terminal segment 202 may be configured to electrically shield the conductive metal protruding from the intermediate segment 204, and electrically terminate the alternative conductor (e.g., the shield conductor 306) within the lead cable 200. For example, the shield segment 205 may include an insulator, such as polyethylene, Tetrafluoroe-thylene, fluorinated ethylene propylene, PVC, Neoprene, and/or the like.

The intermediate segment 204 is between the sensor terminal segment 202 and a splitter junction 206. For example, the intermediate segment 204 may range from 73 to 130 centimeters in length. The intermediate segment 204 may be configured to carry or transmit the electrical signals from the sensors 114 to the combiner connector 112. The intermediate segment 204 may include a non-conductive enclosure 310 (shown in FIG. 3), such as a PVC jacket, to electrically shield the sensor conductor 302. Additionally, in connection with FIG. 3, the intermediate segment 204 may include opposing linear surfaces 320 and 322.

Figure 3:
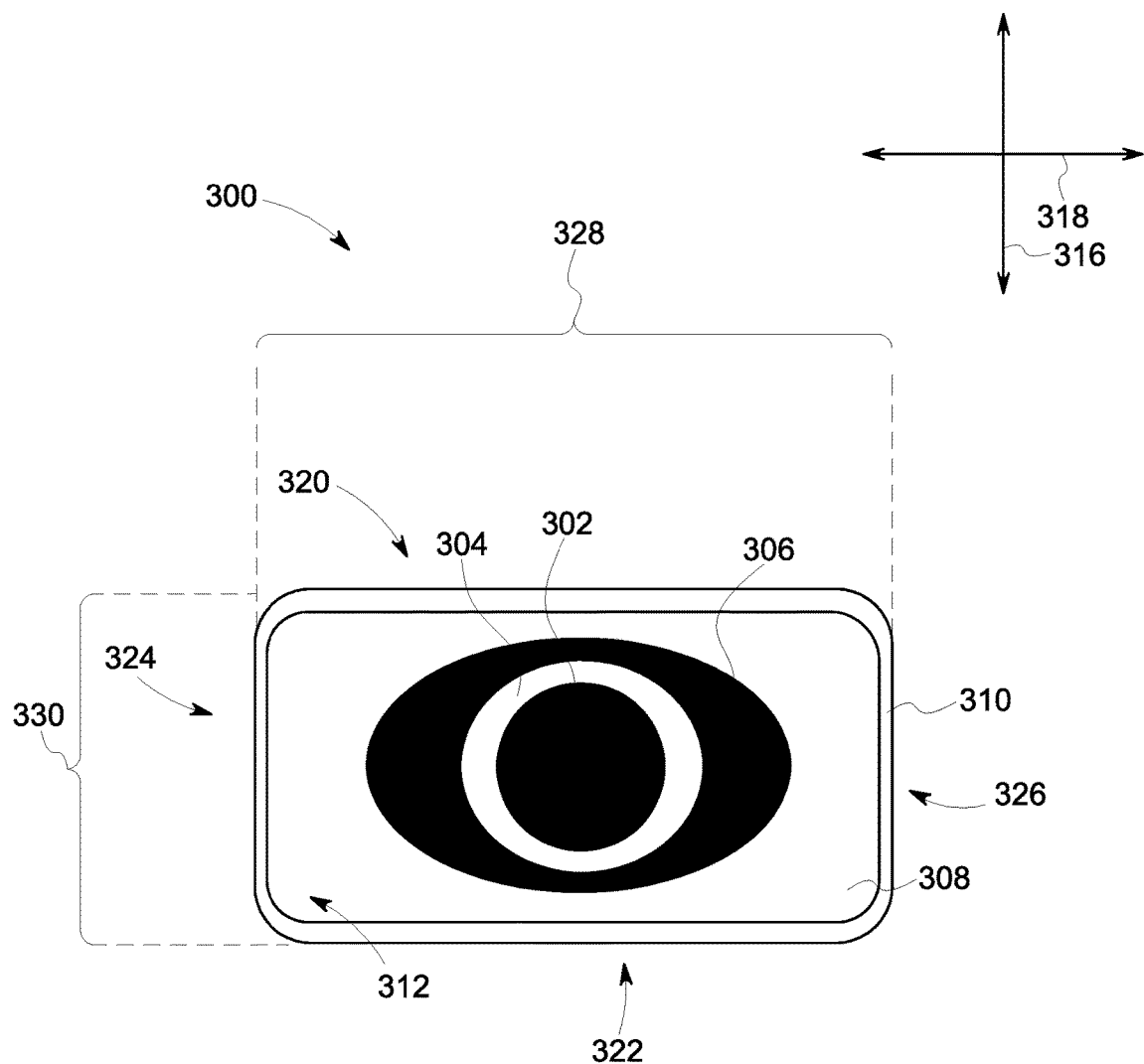
FIG. 3 illustrates a cross section of an intermediate segment of the lead cable shown in FIGS. 2A-B, in accordance with an embodiment.

FIG. 3 illustrates a cross section 300 of the intermediate segment 204 of the lead cable 200, in accordance with an embodiment. The sensor conductor 302 may be centrally located within the intermediate segment 204 surrounded by an insulator 304. The sensor conductor 302 may carry or transmit the electrical signal generated by the sensor 114, coupled to the sensor terminal 203 the opposing sensor terminal 214. The sensor conductor 302 may be a conductive metal such as nickel, copper, gold, silver, tin, conductive alloy, and/or the like. The intermediate segment 204 may be configured to electromagnetically shield or protect the electrical signals traversing along the sensor conductor 302. In various embodiment, the intermediate segment 204 includes components to electrically shield the sensor conductor 302. For example, the intermediate segment 204 includes an insulator 304 and the shield conductor 306.

The insulator 304 is interposed between the sensor conductor 302 and the shield conductor 306. For example, the insulator 304 may surround an outer surface of the sensor conductor 302 extending from the sensor terminal segment 202 to the splitter junction 206. The insulator 304 may be a solid or foam dielectric such as a polyethylene dielectric, fluorinated ethylene propylene, Teflon, butyl rubber, and/or the like. The insulator 304 may be configured to electrically isolate the sensor conductor 302 from the shield conductor 306.

The shield conductor 306 may be a conductive metal such as aluminum, nickel, copper, gold, silver, tin, conductive alloy, and/or the like. The shield conductor 306 may surround an outer surface area of the insulator 304. For example, the shield conductor 306 may be formed as a thin foil (e.g., foil shield, bonded foil), a braided shield, a combination thereof, and/or the like that surrounds the insulator 304. In various embodiments, the shield conductor 306 may be electrically coupled to a ground or common of the ECG system 100.

It may be noted that the electrical properties (e.g., the characteristic impedance, capacitance, propagation velocity, and/or the like) of the intermediate segment 204 may be based on the relative geometries of the shield conductor 306 to the sensor conductor 302, length of the intermediate segment 204, a dielectric constant of the insulator 304, and/or the like. In various embodiments, the geometries of the shield conductor 306 and the sensor conductor 302 may be configured to generate electrical properties of the intermediate segment 204 to be in accordance with Title 21 C.F.R. Section Part 898 entitled Performance Standard for Electrode Lead Wire and Patient Cables.

The non-conductive enclosure 310 may enclose the shield conductor 306. The non-conductive enclosure 310 may be a housing or jacket that protects the components of the intermediate segment 204 (e.g., the shield conductor 306, the insulator 304, the sensor conductor 302, and/or the like). The non-conductive enclosure 310 may include polyethylene, Tetrafluoroe-thylene, fluorinated ethylene propylene, PVC, Neoprene, and/or the like. In various embodiments, a second insulator 312 may be interposed between the non-conductive enclosure 310 and the shield conductor 306. Additionally or alternatively, the shield conductor 306 may be shaped similarly to the non-conductive enclosure 310. For example, the non-conductive enclosure 310 may be directly adjacent to and surround a surface area of the shield conductor 306.

The non-conductive enclosure 310 may additionally form a shape or form factor of the intermediate segment 204. In various embodiments, the non-conductive enclosure 310 may be a quadrilateral. For example, as shown in FIG. 3, the non-conductive enclosure 310 may have a generally rectangular shape. The non-conductive enclosure 310 includes opposing linear surfaces 320 and 322 have a substantially planar shape. For example, at least twenty percent of the opposing linear surfaces 320 and 322 are flat. The opposing linear surfaces 320 and 322 may be in parallel with respect to each other. For example, the opposing linear surface 320 and 322 may be aligned along a horizontal plane 318. Extending along curved edges from the linear surface 320 to the linear surface 322 are opposing lateral surfaces 324 and 326. Additionally or alternatively, the lateral surfaces 324 and 326 may be orthogonal (e.g., right angle) to the opposing linear surfaces 320 and 322. Optionally, the lateral surfaces 324 and 326 may be in parallel with each other. For example, the lateral surfaces 324 and 326 are aligned along a vertical plane 316.

As shown in FIG. 3, a length 328 of the opposing linear surfaces 320 and 322 may be longer relative to a length 330 of the lateral surfaces 324 and 326. In various embodiments, a ratio between the lengths 328 and 330 may be greater than one to provide a flat profile of the intermediate segment 204. For example, the length 328 may correspond to a width of the intermediate segment 204 (e.g., shown in FIG. 2A) and the length 330 may correspond to a height of the intermediate segment 204 (e.g., shown in FIG. 2B). Optionally, the ratio between the lengths 328 and 330 may provide a flat profile of the intermediate section 204. For example, the ratio may be over 10 such that the length 328 is ten times longer than the length 330. It should be noted that in various other embodiments the non-conductive enclosure 310 may form other shapes (e.g., non-conductive enclosures 404, 432, 462 shown in FIG. 4, non-conductive enclosures 534 and 564 shown in FIG. 5) and/or have different length ratios.

Returning to FIGS. 2A-B, the splitter junction 206 may be positioned between the intermediate segment 204 and the combiner terminal segment 208. The splitter junction 206 may partition or separate the sensor conductor 302 and the shield conductor 306 from the intermediate segment 204. For example, the splitter junction 206 may be configured to direct the sensor conductor 302 into a first arm shield segment 210 and the shield conductor 306 into a second arm shield segment 212 of the combiner terminal segment 208. The splitter junction 206 may further include an insulator configured to electrically isolate the sensor conductor 302 from the shield conductor 306. For example, the insulator may surround or enclose the sensor conductor 302 when traversing from the intermediate segment 204 through the splitter junction 206 into the first arm shield segment 210. In another example, the insulator may surround or enclose the shield conductor 306 when traversing from the intermediate segment 204 through the splitter junction 206 into the second arm shield segment 212.

The first arm shield segment 210 may enclose the sensor conductor 302, and the second arm shield segment 212 may enclose the shield conductor 306. The first and second arm shield segments 210 and 212 may be configured to electrically shield the sensor conductor 302 and the shield conductor 306, respectively. For example, the first and second arm shield segments 210 and 212 may include an insulator, such as polyethylene, Tetrafluoroe-thylene, fluorinated ethylene propylene, PVC, Neoprene, and/or the like.

The combiner terminal segment 208 includes the opposing sensor terminal 214 and a shield terminal 216. Optionally, the combiner terminal segment 208 may be enclosed in a housing (not shown) that is configured to physically couple the combiner terminal segment 208 to the combiner connector 112. The opposing sensor terminal 214 and the shield terminal 216 may include a conductive metal (e.g., nickel, copper, gold, silver, tin, conductive alloy, and/or the like) corresponding to the sensor conductor 302 and the shield conductor 306, respectively.

Figure 4:
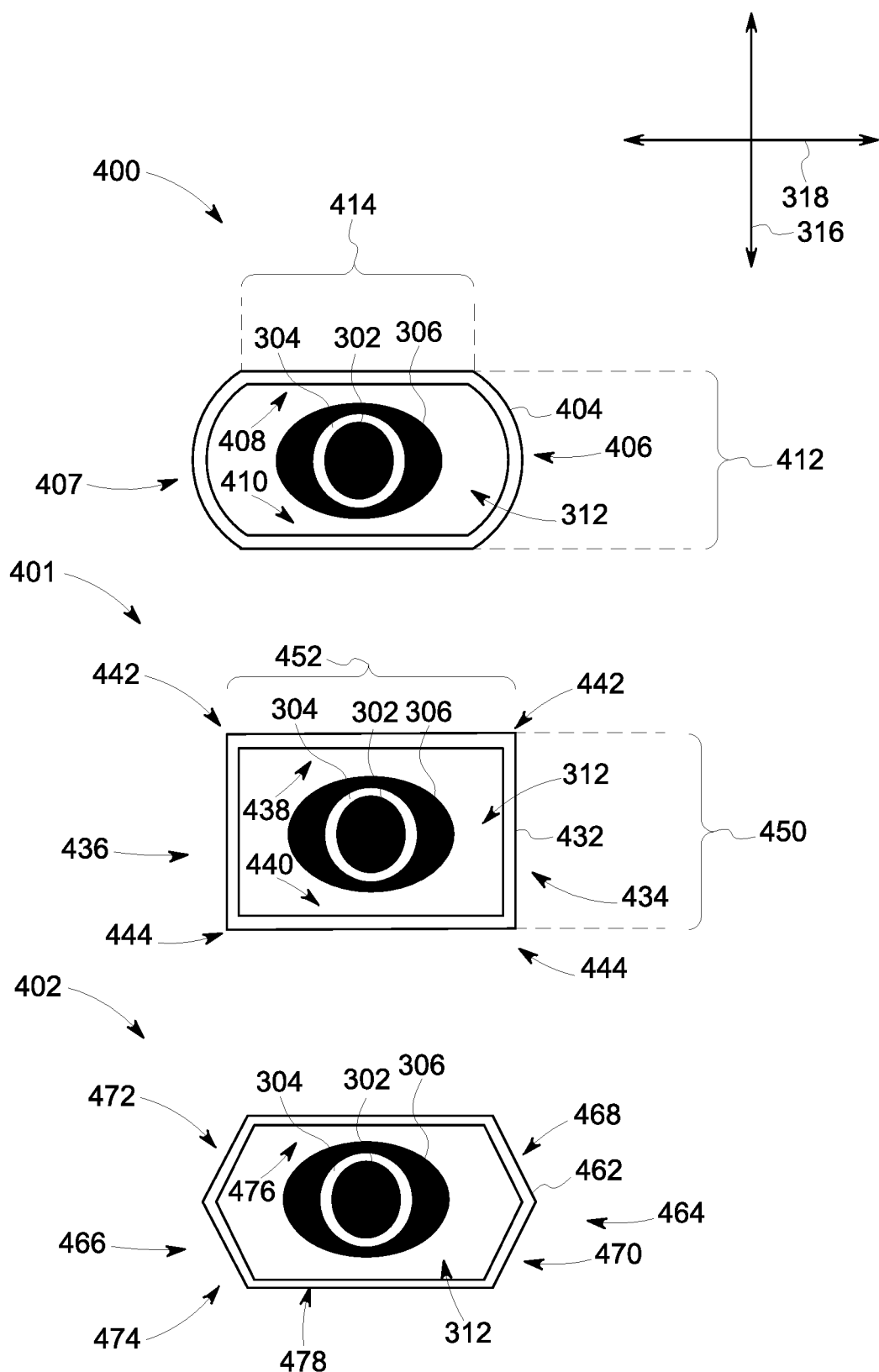
FIG. 4 illustrates cross sections of alternatively shaped intermediate segments of the lead cable shown in FIG. 2, in accordance with various embodiments.

FIG. 4 illustrates cross sections 400-403 of alternatively shaped intermediate segments 204 of the lead cable 200, in accordance with various embodiments. The cross sections 400-402 each include a non-conductive enclosure 404, 432, 462 with opposing linear surfaces 408-410, 438-440 and 476-478. For example, the cross section 400 includes the opposing linear surfaces 408 and 410. In another example, the cross section 401 includes the opposing linear surfaces 438 and 440. In another example, the cross section 402 includes the opposing linear surfaces 476 and 478. The opposing linear surfaces 408-410, 438-440 and 476-478 may be in parallel with respect to each other. Additionally, the opposing linear surfaces 408-410, 438-440, and 476-478 may be similar to or the same as the opposing linear surfaces 320 and 322 shown in FIG. 3. For example, the opposing linear surfaces 408-410, 438-440 and 476-478 may be aligned along the horizontal plane 318.

In connection with the cross section 400, extending from the linear surface 408 to the linear surface 410 are opposing curved surfaces 406 and 407. The curved surfaces 406 and 407 with the opposing linear surfaces 408 and 410 may form a generally oval shape of the non-conductive enclosure 404. A length 414 of the opposing linear surfaces 408 and 410 may be longer relative to a length 412 of the curved surfaces 406 and 407. For example, a ratio between the lengths 414 and 412 may be greater than one to provide a flat profile of the intermediate segment 204.

In connection with the cross section 401, extending orthogonally from the linear surface 438 to the linear surface 440 are opposing lateral surfaces 434 and 436. For example, the cross section 401 includes right angle or orthogonal edges 442-444 extending from the linear surfaces 438 and 440, respectively. The opposing lateral surfaces 434 and 436 may be in parallel with each other. For example, the lateral surfaces 434 and 436 are aligned along the vertical plane 316. Optionally, as shown with respect to the cross section 401, a ratio between lengths 450-452 may be approximately the same. For example, the length 452 of the opposing linear surfaces 438 and 440 may be similar to or the same as the length 450 of the opposing lateral surfaces 434 and 436 to form a generally square shape of the non-conductive enclosure 432. It may be noted, that in other embodiments the length 452 may be different relative to the length 450.

In connection with the cross section 402, extending non-orthogonally from the linear surface 476 to the linear surface 478 are opposing lateral surfaces 464 and 466. The opposing lateral surfaces 464 and 466 are subdivided into a plurality of linear segments 468-474. For example, the lateral surface 464 includes the linear segments 468 and 470, and the lateral surface 466 includes the linear segments 472 and 474 to form a generally hexagon shape of the non-conductive enclosure 462. It may be noted in other embodiments, the opposing lateral surfaces 464 and 466 may each include more than two linear segments 468-474.

It may be noted that in various embodiments, shapes of the intermediate segment 204 (shown in FIG. 2) for each of the lead cables 112 (shown in FIG. 1) may be the same or different with respect to each other.

Figure 5:
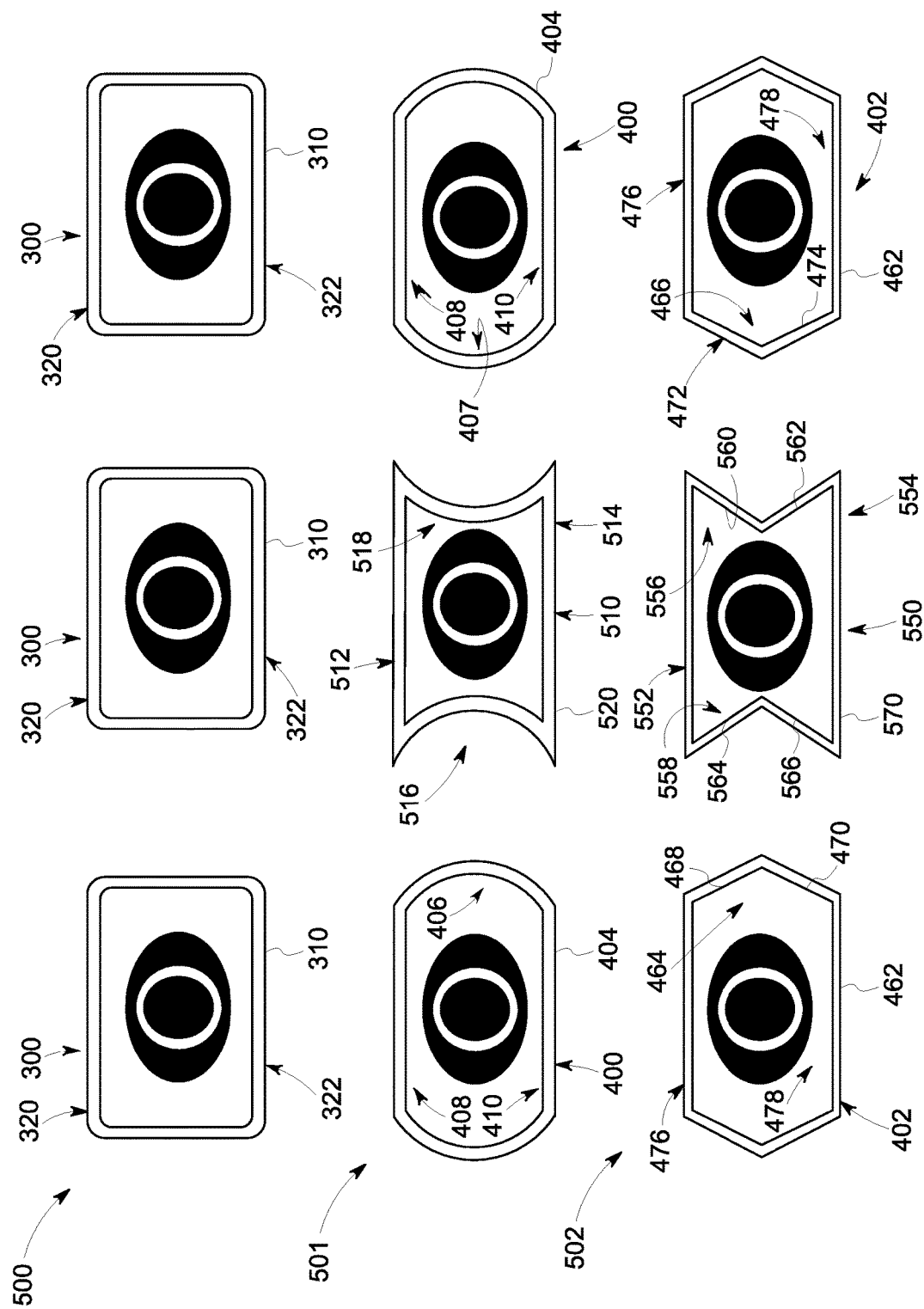
FIG. 5 illustrates sets of cross sections of intermediate segments of lead cables, in accordance with various embodiments.

FIG. 5 illustrates sets 500-502 of cross sections 300, 400, 402, 510 and 550 of various intermediate segments of the lead cables 112, in accordance with various embodiments. For example, the set 500 may represent the cross sections 300 of a plurality of intermediate segments (e.g., the intermediate segment 204) of at least a portion of the lead cables 112 shown in FIG. 1. The opposing linear surfaces 320-322 of the cross sections 300 may enable the lead cables 112 to align along a horizontal plane. For example, the opposing linear surfaces 320-322 of the cross sections 300 may allow the non-conductive enclosures 310 of each lead cable 112 to be aligned with each other such that the linear surfaces 320 and 322 form a first and second horizontal planes, respectively.

Additionally or alternatively, the shapes of the cross sections 400, 402, 510, and 550 with the set 501-502 may be different. For example, the shapes of the cross sections 510, 550 may be configured based on an adjacent cross section 400, 402. The set 501 may represent the cross sections 400 and 510 of a plurality of intermediate segments (e.g., the intermediate segment 204) of at least a portion of the lead cables 112 shown in FIG. 1. For example, a first set of the lead cables 112 that include a non-conductive enclosure 510 of the cross section 510 may be interposed between a second set of the lead cables 112 that include the non-conductive enclosure 404.

The non-conductive enclosure 510 includes opposing linear surfaces 512 and 514. The opposing linear surfaces 512 and 514 may be in parallel with respect to each other. Additionally, the opposing linear surfaces 512 and 514 may be similar to or the same as the opposing linear surfaces 408 and 410 shown in FIG. 4. For example, the opposing linear surfaces 408-410 and 512-514 of the cross sections 400 and 510, respectively, may enable first and second sets of the lead cables 112 to align along the same horizontal plane.

Additionally, the non-conductive enclosure 510 may be configured based on the shape of the non-conductive enclosures 404. For example, the non-conductive enclosure 510 includes opposing curved surfaces 516 and 518. A shape of the opposing curved surfaces 516 and 518 are based on the opposing curved surfaces 406 and 407 of the non-conductive enclosure 400. For example, the opposing curved surfaces 406 and 407 may be mirrored by the opposing curved surfaces 516 and 518. Additionally or alternatively, a shape of the opposing curved surfaces 516 and 518 may be configured to be an inverse of the shape of the opposing curved surfaces 406 and 407. Optionally, the non-conductive enclosure 510 may be configured to receive the adjacent opposing curved surfaces 406 and 407. For example, the opposing curved surfaces 406 and 407 may be directly adjacent or in contact with the opposing curved surfaces 516 and 518, respectively, when the opposing linear surfaces 408-410 and 512-514 are aligned along the horizontal plane. Additionally, when the non-conductive enclosure 510 receives the opposing curved surfaces 406 and 407, at least a portion of the curved surface 406 and/or the curved surface 407 are interposed between the opposing linear surfaces 512-514.

In another example, the set 502 may represent the cross sections 402 and 550 of a plurality of intermediate segments (e.g., the intermediate segment 204) of at least a portion of the lead cables 112 shown in FIG. 1. For example, a first set of the lead cables 112 that include a non-conductive enclosure 570 of the cross section 550 may be interposed between a second set of the lead cables 112 that include the non-conductive enclosure 462.

The non-conductive enclosure 550 includes opposing linear surfaces 552 and 554. The opposing linear surfaces 552 and 554 may be in parallel with respect to each other. Additionally, the opposing linear surfaces 552 and 554 may be similar to or the same as the opposing linear surfaces 476 and 478 shown in FIG. 4. For example, the opposing linear surfaces 476-478 and 552-554 of the cross sections 402 and 550, respectively, may enable first and second sets of the lead cables 112 to align along the same horizontal plane.

Additionally, the non-conductive enclosure 570 may be configured based on the shape of the non-conductive enclosures 462. For example, the non-conductive enclosure 570 includes opposing lateral surfaces 556 and 558. A shape of the opposing lateral surfaces 556 and 558 are based on the opposing lateral surfaces 464 and 466 of the non-conductive enclosure 462. For example, the opposing lateral surfaces 464-466 and 556-558 may each include the same number of linear segments 468-474 and 560-566. In another example, the opposing lateral surfaces 464 and 466 may be mirrored by the opposing lateral surfaces 566 and 568. Additionally or alternatively, the linear segments 560-566 of the opposing lateral surfaces 516 and 518 may be configured to be positioned inversely relative to the linear segments 468-474 of the opposing curved surfaces 464 and 466. Optionally, the non-conductive enclosure 570 may be configured to receive the adjacent opposing lateral surfaces 464 and 466. For example, the opposing lateral surfaces 464 and 466 can be positioned directly adjacent or in contact with the opposing lateral surfaces 516 and 518, respectively, when the opposing linear surfaces 476-478 and 552-554 are aligned along the horizontal plane. Additionally, when the non-conductive enclosure 570 receives the opposing lateral surfaces 464 and 466, at least a portion of the lateral surface 464 (e.g., the linear segments 468, 470) and/or the lateral surface 466 (e.g., the linear segments 472, 474) are interposed between the opposing linear surfaces 552-554.

Figure 6:
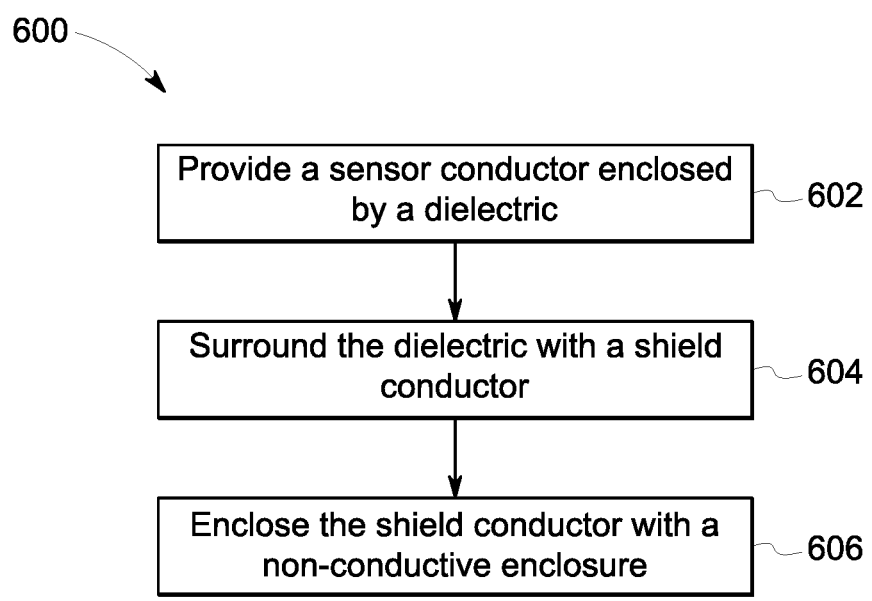
FIG. 6 illustrates a flow chart of a method in accordance with an embodiment.

FIG. 6 is a flow chart of a method 600 in accordance with an embodiment. The method 600 may be, for example, a method of manufacturing or assembling a lead cable. The method 600 may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 600 includes providing, at 602, providing a sensor conductor enclosed by a dielectric. For example, the sensor conductor may be similar to or the same as the sensor conductor 302 shown in FIG. 3. The dielectric may be similar to or the same as the dielectric 304. For example, the dielectric may electrically shield the sensor conductor. The sensor conductor may be configured to carry an electrical signal related to cardiac activity generated by a sensor. For example, the sensor conductor may carry electrical signals generated by a sensor similar to or the same as one of the sensors 114 shown in FIG. 1.

The method 600 includes surrounding the dielectric with a shield conductor. The shield conductor may be similar to or the same as the shield conductor 306 shown in FIG. 3. Additionally or alternatively, the dielectric may be interposed between the dielectric and the shield conductor.

The method 600 also includes enclosing the shield conductor with a non-conductive enclosure. The non-conductive enclosure includes opposing linear surfaces and opposing lateral surfaces extending from the opposing linear surfaces, wherein the opposing linear surfaces are parallel with respect to each other. For example, the non-conductive enclosure may be the non-conductive enclosure 310, 303, 404, 432, 462, 520, or 550.

In one embodiment, a lead cable is provided. The lead cable includes a sensor terminal segment that includes a sensor terminal. The sensor terminal is configured to be electrically coupled to an electrocardiogram sensor. The lead cable further includes a combiner terminal segment that includes an opposing sensor terminal and a shield terminal. The lead cable also includes an intermediate segment interposed between the sensor terminal segment and the combiner terminal segment. The intermediate segment is configured to carry electrical signals generated by the electrocardiogram sensor from the sensor terminal to the opposing sensor terminal. The lead cable further includes non-conductive enclosure configured to house the intermediate segment. The non-conductive enclosure having opposing linear surfaces and opposing lateral surfaces extending from the opposing linear surfaces. The opposing linear surfaces are parallel with respect to each other.

Optionally, a first length of the opposing linear surfaces are different than a second length of the opposing lateral surfaces.

Optionally, a ratio between the first length and the second length is greater than one.

Optionally, a shape of the opposing lateral surfaces are based on a second non-conductive enclosure.

Optionally, the opposing lateral surfaces extend non-orthogonally from the opposing linear surfaces.

Optionally, the opposing lateral surfaces extend orthogonally from the opposing linear surfaces.

Optionally, the opposing lateral surfaces includes a curved surface or a linear surface.

Optionally, the system includes a sensor conductor and shield conductor traversing within the intermediate segment.

Additionally or alternatively, the sensor conductor is electrically coupled to the sensor terminal and the opposing sensor terminal.

Optionally, the combiner terminal is configured to be electrically and physically coupled to a combiner connector.

In an alternative embodiment, a system (e.g., an electrocardiogram system) is provided. The system includes an array of sensors configured to generate electrical signals relating to cardiac activity. The system further includes a plurality of lead cables. Each lead cable includes a sensor terminal, an opposing sensor terminal, and an intermediate segment. The intermediate segment is interposed between the sensor terminal and the opposing sensor terminal. The array of sensors are electrically coupled to the sensor terminals. The intermediate segment is configured to carry the electrical signals from the sensor terminal to the opposing sensor terminal. The intermediate segment is enclosed by a non-conductive enclosure. The non-conductive enclosure having opposing linear surfaces and opposing lateral surfaces extending from the opposing linear surfaces. The opposing linear surfaces are parallel with respect to each other.

Optionally, a first set of the lead cables have first opposing lateral surfaces and a second set of the lead cables have second opposing lateral surfaces. Additionally or alternatively, a shape of the second opposing lateral surfaces are based on a shape of the first opposing lateral surfaces. Additionally or alternatively, the second opposing lateral surfaces are configured to receive the first opposing lateral surfaces.

Optionally, the system includes a combiner connector. The opposing sensor terminal is electrically coupled to the combiner connector. The combiner connector may be configured to combine a first electrical signal received from a first opposing sensor terminal with a second electrical signal received form a second opposing sensor terminal.

Optionally, the opposing lateral surfaces extend non-orthogonally from the opposing linear surfaces.

Optionally, the opposing lateral surfaces extend orthogonally from the opposing linear surfaces.

Optionally, the opposing lateral surfaces includes a curved surface or a linear surface.

Optionally, the intermediate segment includes a shield conductor electrically coupled to a common ground.

Optionally, a first length of the opposing linear surfaces are different than a second length of the opposing lateral surfaces.

In an alternative embodiment, a method (e.g., method for manufacturing a lead cable for an electrocardiogram system) is provided. The method includes providing a sensor conductor enclosed by a dielectric. The sensor conductor is configured to carry an electrical signal related to cardiac activity generated by a sensor. The method also includes surrounding the dielectric with a shield conductor. The dielectric is interposed between the dielectric and the shield conductor. The method further includes enclosing the shield conductor with a non-conductive enclosure. The non-conductive enclosure includes opposing linear surfaces and opposing lateral surfaces extending from the opposing linear surfaces. The opposing linear surfaces are in parallel with respect to each other.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An external surface cable comprising:
an external surface sensor terminal segment that includes a sensor terminal, wherein the sensor terminal is configured to be electrically coupled to an external surface electrocardiogram sensor;
a combiner terminal segment that includes an opposing sensor terminal and a shield terminal;
an intermediate segment interposed between the external surface sensor terminal segment and the combiner terminal segment, the intermediate segment configured to carry electrical signals generated by the external surface electrocardiogram sensor from the sensor terminal to the opposing sensor terminal; and
a non-conductive enclosure configured to house the intermediate segment, the non-conductive enclosure having opposing linear surfaces aligned along a first plane to provide a flat profile and opposing lateral surfaces extending from the opposing linear surfaces, wherein the opposing linear surfaces are parallel with respect to each other.

2. The lead cable of claim 1, wherein the opposing linear surfaces have a first length that extends along the first plane and corresponds to a width of the intermediate segment, the first length of the opposing linear surfaces is longer than a second length of the opposing lateral surfaces to provide the flat profile.

3. The lead cable of claim 1, wherein the opposing lateral surfaces extend non-orthogonally from the opposing linear surfaces, the opposing lateral surfaces having a length, aligned along a vertical plane, that corresponds to a height of the intermediate segment to at least partially avoid twisting and/or knotting of a plurality of the external surface lead cables.

4. The lead cable of claim 1, wherein the opposing lateral surfaces extend orthogonally from the opposing linear surfaces to form a planar shape.

5. The lead cable of claim 1, wherein the opposing lateral surfaces includes a curved surface or a linear surface.

6. The lead cable of claim 1, further comprising a sensor conductor and shield conductor traversing within the intermediate segment, the sensor conductor electrically coupled to the sensor terminal and the opposing sensor terminal.

7. The lead cable of claim 1, wherein the opposing linear surfaces have a first length aligned along a horizontal axis and the opposing lateral surfaces have a second length aligned along a vertical axis, wherein a ratio between the first and second lengths is greater than one to provide the flat profile to at least partially avoid twisting and/or knotting of first and second external surface lead cables.

8. The lead cable of claim 1, wherein the intermediate segment comprises a sensor conductor and shield conductor separated by a dielectric, the opposed linear surfaces extend along a plane by a length that is great than a width of the shield conductor.

9. An external surface lead cable comprising:
an external surface sensor terminal segment that includes a sensor terminal, wherein the sensor terminal is configured to be electrically coupled to an external surface electrocardiogram sensor;
a combiner terminal segment that includes an opposing sensor terminal and a shield terminal;
an intermediate segment interposed between the external surface sensor terminal segment and the combiner terminal segment, the intermediate segment configured to carry electrical signals generated by the external surface electrocardiogram sensor from the sensor terminal to the opposing sensor terminal; and
a non-conductive enclosure configured to house the intermediate segment, the non-conductive enclosure having opposing linear surfaces and opposing lateral surfaces extending from the opposing linear surfaces, wherein the opposing linear surfaces are parallel with respect to each other, wherein a first shape of the opposing lateral surfaces are based on a second shape of a second non-conductive enclosure.

10. The lead cable of claim 9, wherein the first and second shapes are configured to receive each other to align along a horizontal axis to at least partially avoid twisting and/or knotting of first and second external surface lead cables.

11. An external surface electrocardiogram system comprising:
an array of external surface sensors configured to generate electrical signals relating to cardiac activity;

a plurality of external surface lead cables, wherein each external surface lead cable includes a sensor terminal, an opposing sensor terminal, and an intermediate segment, the intermediate segment is interposed between the sensor terminal and the opposing sensor terminal, wherein the array of external surface sensors are electrically coupled to the sensor terminals, the intermediate segment configured to carry the electrical signals from the sensor terminal to the opposing sensor terminal, the intermediate segment is enclosed by a non-conductive enclosure, the non-conductive enclosure having opposing linear surfaces aligned along a first plane to provide a flat profile and opposing lateral surfaces extending from the opposing linear surfaces, wherein the opposing linear surfaces are parallel with respect to each other.

12. The electrocardiogram system of claim 11, wherein a first set of the external surface lead cables have first opposing lateral surfaces and a second set of the external surface lead cables have second opposing lateral surfaces, the first opposing lateral surfaces having a first shape that is mirrored by a second shape of the second opposing lateral surfaces to at least partially avoid twisting and/or knotting of the first and second sets of the external surface lead cables.

13. The electrocardiogram system of claim 12, wherein a first shape of the first opposing lateral surfaces is an inverse of the second shape of the second opposing lateral surfaces.

14. The electrocardiogram system of claim 13, wherein the first shape of the first opposing lateral surfaces has a curved shape that is an inverse to a curved shape of the second shape of the second opposing lateral surfaces.

15. The electrocardiogram system of claim 11, further comprising a combiner connector, wherein the opposing sensor terminal is electrically coupled to the combiner connector, the combiner connector configured to combine a first electrical signal received from a first opposing sensor terminal with a second electrical signal received form a second opposing sensor terminal.

16. The electrocardiogram system of claim 11, wherein the opposing lateral surfaces extend non-orthogonally from the opposing linear surfaces.

17. The electrocardiogram system of claim 11, wherein the opposing lateral surfaces extend orthogonally from the opposing linear surfaces.

18. The electrocardiogram system of claim 11, wherein the opposing lateral surfaces includes a curved surface or a linear surface.

19. The electrocardiogram system of claim 11, wherein the intermediate segment includes a shield conductor electrically coupled to a common ground.

20. The electrocardiogram system of claim 11, wherein a first length of the opposing linear surfaces are longer than a second length of the opposing lateral surfaces to provide the flat profile, the first length corresponding to a width of the intermediate segment.

21. The electrocardiogram system of claim 11, wherein the intermediate segment, of at least a portion of the plurality of lead cables, comprises a sensor conductor and shield conductor separated by a dielectric, the opposed linear surfaces extend along a plane by a length that is great than a width of the shield conductor to at least partially avoid twisting and/or knotting between the plurality of lead cables.

22. A method for manufacturing an external surface lead cable for an electrocardiogram system, the method comprising:
    providing a sensor conductor enclosed by a dielectric, wherein the sensor conductor is configured to carry an electrical signal related to cardiac activity generated by an external surface sensor;
    surrounding the dielectric with a shield conductor, wherein the dielectric is interposed between the dielectric and the shield conductor; and
    enclosing the shield conductor with a non-conductive enclosure, wherein the non-conductive enclosure includes opposing linear surfaces aligned along a first plane to provide a flat profile and opposing lateral surfaces extending from the opposing linear surfaces, wherein the opposing linear surfaces are in parallel with respect to each other.

23. The method of claim 22, wherein the intermediate segment comprises a sensor conductor and shield conductor separated by a dielectric, the opposed linear surfaces extend along a plane by a length that is great than a width of the shield conductor to at least partially avoid twisting and/or knotting of first and second external surface lead cables.

* * * * *